(12) United States Patent
Flament et al.

(10) Patent No.: US 6,180,848 B1
(45) Date of Patent: Jan. 30, 2001

(54) PROSTHESIS OBTURATING DEVICE FOR THE OBTURATION OF A HERNIAL CANAL

(75) Inventors: Jean Bernard Flament, Taissy; Axel Arnaud, Neuilly sur Seine, both of (FR)

(73) Assignees: Ethicon, Inc., Somerville, NJ (US); Ethicon, S.A.S. (FR)

(*) Notice: Under 35 U.S.C. 154(b), the term of this patent shall be extended for 0 days.

(21) Appl. No.: 09/139,197

(22) Filed: Aug. 25, 1998

(30) Foreign Application Priority Data

Aug. 27, 1997 (FR) .................................................. 97 10697

(51) Int. Cl.⁷ .............................. A61F 2/02; A61B 17/00
(52) U.S. Cl. ........................... 623/11; 606/151; 606/153; 606/213
(58) Field of Search .............................. 623/11; 606/213, 606/151, 153

(56) References Cited

U.S. PATENT DOCUMENTS

| | | |
|---|---|---|
| 636,952 | 11/1899 | Chaney . |
| 2,683,136 | 7/1954 | Higgins ............................... 260/78.3 |
| 2,761,444 | 9/1956 | Luck ..................................... 128/92 |
| 3,054,406 | 9/1962 | Usher .................................. 128/334 |
| 3,124,136 | 3/1964 | Usher .................................. 128/334 |
| 3,707,150 | 12/1972 | Montgomery et al. .......... 128/334 R |
| 3,874,388 | 4/1975 | King et al. ...................... 128/334 R |
| 4,007,743 | 2/1977 | Blake ............................... 128/334 R |
| 4,013,569 | 3/1977 | Chiu et al. ...................... 252/8.55 D |

(List continued on next page.)

FOREIGN PATENT DOCUMENTS

| | | | |
|---|---|---|---|
| 0 544 485 B1 | 11/1992 | (EP) | ................................ A61B/17/00 |
| 0 537 769 A1 | 4/1993 | (EP) | ................................ A61L/31/00 |
| 0 544 485 A1 | 6/1993 | (EP) | ................................ A61B/17/00 |
| 0 614 650 A2 | 2/1994 | (EP) | ................................ A61F/2/00 |
| 0 614 650 A2 | 9/1994 | (EP) | ................................ A61F/2/00 |
| 0 677 297 A1 | 10/1995 | (EP) | ................................ A61L/27/00 |
| 0 692 225 A2 | 1/1996 | (EP) | ................................ A61F/2/00 |
| 0 698 395 A1 | 2/1996 | (EP) | ................................ A61L/27/00 |
| 0 719 527 A1 | 7/1996 | (EP) | ................................ A61F/2/00 |
| 0 744 162 A2 | 11/1996 | (EP) | ................................ A61F/2/00 |
| 0 537 955 B1 | 12/1996 | (EP) | ................................ A61B/17/12 |
| 0 797 962 A2 | 10/1997 | (EP) | ................................ A61F/2/00 |
| WO 90/14796 | 12/1990 | (WO) | ................................ A61B/17/12 |
| WO 92/06639 | 4/1992 | (WO) | ................................ A61B/17/00 |
| WO 92/13500 | 8/1992 | (WO) | ................................ A61F/2/02 |
| WO 92/19162 | 11/1992 | (WO) | ................................ A61B/17/04 |
| WO 93/03685 | 3/1993 | (WO) | ................................ A61F/2/00 |
| WO 93/17635 | 9/1993 | (WO) | ................................ A61F/2/00 |
| WO 94/17747 | 8/1994 | (WO) | ................................ A61B/19/00 |
| WO 94/27535 | 12/1994 | (WO) | ................................ A61F/13/00 |
| WO 95/07666 | 3/1995 | (WO) | ................................ A61F/2/02 |
| WO 95/13762 | 5/1995 | (WO) | ................................ A61F/2/02 |
| WO 95/31140 | 11/1995 | (WO) | ................................ A61B/17/00 |
| WO 95/32687 | 12/1995 | (WO) | ................................ A61F/2/00 |
| WO 96/03091 A1 | 2/1996 | (WO) | ................................ A61F/2/00 |
| WO 96/03165 A1 | 2/1996 | (WO) | ................................ A61L/31/00 |
| WO 96/09795 | 4/1996 | (WO) | ................................ A61B/17/00 |
| WO 96/14805 | 5/1996 | (WO) | ................................ A61F/2/00 |
| WO 96/41588 | 12/1996 | (WO) | ................................ A61F/2/00 |
| WO 97/02789 | 1/1997 | (WO) | ................................ A61F/2/00 |
| WO 97/22310 | 6/1997 | (WO) . | |

*Primary Examiner*—David J. Isabella
*Assistant Examiner*—Choon P. Koh

(57) ABSTRACT

The invention concerns a prosthesis obturating device to obturate a hernial canal comprising, a part (1) made of sheet material for extending through the hernial canal and being characterized in that this first part is extended, at its end that is to be adjacent to the hernial cavity, inside this hernial cavity, by a second part, also made of sheet material and for covering the internal orifice of the hernial canal.

13 Claims, 1 Drawing Sheet

U.S. PATENT DOCUMENTS

| | | | |
|---|---|---|---|
| 4,347,847 | 9/1982 | Usher | 128/334 |
| 4,548,202 | 10/1985 | Duncan | 128/334 |
| 4,633,873 | 1/1987 | Dumican et al. | 128/334 |
| 4,769,038 | 9/1988 | Bendavid et al. | 623/13 |
| 4,854,316 | 8/1989 | Davis | 128/334 R |
| 4,917,089 | 4/1990 | Sideris | 606/215 |
| 5,002,551 | 3/1991 | Linsky et al. | 606/151 |
| 5,021,059 | 6/1991 | Kensey et al. | 606/213 |
| 5,092,884 | 3/1992 | Devereux et al. | 623/11 |
| 5,108,420 * | 4/1992 | Marks | 606/213 |
| 5,108,421 | 4/1992 | Fowler | 606/213 |
| 5,108,520 | 4/1992 | Marks | 606/213 |
| 5,116,357 | 5/1992 | Eberbach | 606/213 |
| 5,122,155 | 6/1992 | Eberbach | 606/213 |
| 5,141,515 | 8/1992 | Eberbach | 606/151 |
| 5,147,374 | 9/1992 | Fernandez | 606/151 |
| 5,171,148 | 12/1992 | Wasserman et al. | 433/215 |
| 5,219,077 | 6/1993 | Transue . | |
| 5,246,455 | 9/1993 | Shikani | 623/10 |
| 5,249,682 | 10/1993 | Transue | 206/438 |
| 5,254,133 * | 10/1993 | Seid | 606/215 |
| 5,258,000 | 11/1993 | Gianturco . | |
| 5,292,328 | 3/1994 | Hain et al. | 606/151 |
| 5,297,714 | 3/1994 | Kramer | 227/175 |
| 5,316,543 | 5/1994 | Eberbach | 600/37 |
| 5,334,217 | 8/1994 | Das . | |
| 5,350,399 * | 9/1994 | Erlebacher et al. | 606/213 |
| 5,356,432 | 10/1994 | Rutkow et al. | 623/11 |
| 5,366,460 | 11/1994 | Eberbach | 606/151 |
| 5,370,650 | 12/1994 | Tovey et al. . | |
| 5,397,331 | 3/1995 | Himpens et al. | 606/151 |
| 5,397,332 | 3/1995 | Kammerer et al. | 606/151 |
| 5,456,720 | 10/1995 | Schultz et al. | 623/12 |
| 5,569,273 | 10/1996 | Titone et al. | 606/151 |
| 5,578,045 | 11/1996 | Das | 606/151 |
| 5,634,944 * | 6/1997 | Magram | 623/11 |
| 5,686,090 | 11/1997 | Schilder et al. | 424/423 |

* cited by examiner

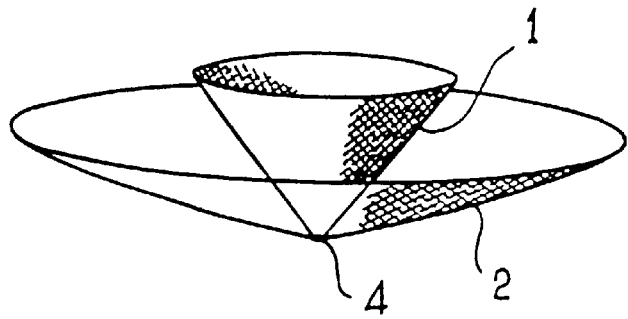
FIG_1
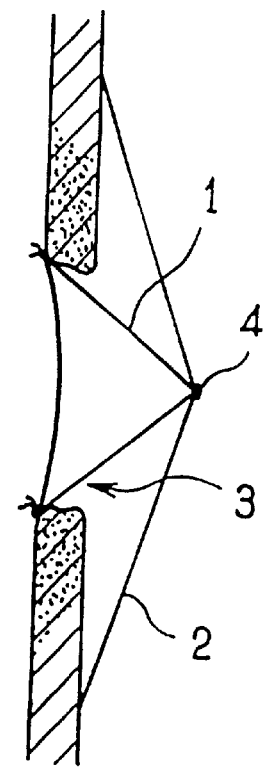
FIG_2
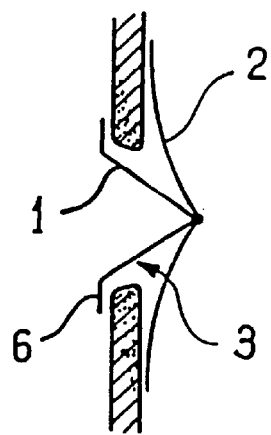
FIG_3
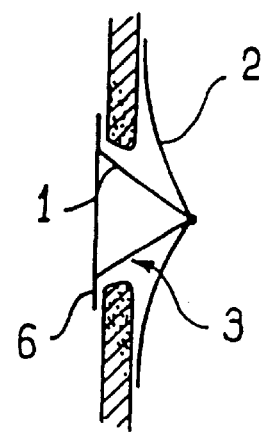
FIG_4

PROSTHESIS OBTURATING DEVICE FOR THE OBTURATION OF A HERNIAL CANAL

The present invention relates to a prosthesis obturating device used to obturate a hernial canal.

In conventional techniques, hernial canal repair is generally carried out by suturing. However, that method of repair is not entirely satisfactory: given that the suture line is subject to a large amount of tension, there is a risk of tearing, which could then lead to recurrence of the hernia. Further, even in the absence of tearing, any tension is synonimous of post-operating pain for the patient.

In order to mitigate that disadvantage, tension-free hernia repair techniques have been proposed.

In particular, a known technique is to position a sheet of synthetic prosthesis material, of tulle mesh or analogous type, at the superficial orifice of the hernial canal, to reinforce or replace the weakened tissue. For example, in open surgical repair of an inguinal hernia, a piece may be used which is positioned on the inguinal ring, on the side remote from the peritoneum, this band being slit to allow the spermatic cord to pass, and the two tails of the band are then wound around the spermatic cord. The barrier thus created makes it possible for the inguinal canal floor to regenerate.

Such a barrier-forming patch may also be positioned by non-invasive surgery. A device using a trocar to deploy prosthesis sheets inside the abdominal cavity, on the peritoneum, is described in EP 0 544 485, for example.

Another tension-free repair technique, which may be used in combination with the above-mentioned consists in obturating the hernial orifice with a prosthesis or obturating device.

Usually a surgeon makes an obturating device by rolling a patch cut out from prosthesis material in order to obtain a cylinder of appropriate dimensions.

Other shapes of prosthesis obturating devices are also used, such as rectangular obturators, conical obturators or collared obturators enabling them to be positioned relative to the hernial orifice. The following may be consulted in that respect:

"Prosthesis and Abdominal Wall Hernias", Robert Bendavid, RG Landes Company, Austin, pages 375–379, 380–382, 383–388, 389–398, 408–410, 411–412, 413–414, 446–449, and also U.S. Pat. No. 5,116,357 and U.S. Pat. No. 5,356,432.

Other known prostheses are constituted by cylindrical obturators terminating at one end with prosthesis sheets for suturing by the surgeon to the non-weakened muscles on either side of the hernial orifice to complement the obturation provided by the obturator. In that respect reference may advantageously be made to U.S. Pat. No. 5,219,077 and U.S. Pat. No. 5,249,682, for example.

The object of the invention is to propose a prosthesis obturating device which is simple in structure and simple to manipulate and which is also very efficient.

The invention therefore provides a prosthesis obturating device to obturate a hernial canal comprising a part made of sheet(s) material for extending through the hernial canal and being characterized in that this first part is extended, at its end that is to be adjacent to the hernial cavity (abdominal cavity), inside this hernial cavity, by a second part, also made of sheet material and for covering the internal orifice of the hernial canal.

Given this structure, the first part which is inserted in the hernial canal to obturate it, is reinforced by a barrier-forming part which, because it is positioned on the inside of the hernial cavity and not on the outside, presents very good resistance to the abdominal pressure inside the hernial cavity.

Other characteristics and advantages of the invention can be seen from the following description. This description is intended as an illustration and is not limiting. It shall be read in consultation with the accompanying drawing where:

FIG. 1 is a perspective diagram of a prosthesis obturating device in one possible embodiment of the invention;

FIG. 2 is a cross-section diagram showing the position of the obturating device in FIG. 1 in the hernial canal;

FIG. 3 is a perspective view of another equally possible variant of the invention; and FIG. 4 is a cross-sectional view similar to that of FIG. 2 of another equally possible embodiment.

The obturating device illustrated in FIGS. 1 and 2 comprises two main parts: one, referenced 1 constitutes the obturator proper; the other, referenced 2, is constituted by a prosthesis sheet to be positioned inside the hernial cavity to constitute a barrier at the internal orifice of the hernial canal, said canal being referenced 3 in FIG. 2.

By way of example, the general shape of the obturating-forming part 1 is cylindrical or conical as is shown in the drawing.

More precisely, the part 1 is preferentially hollow and made for example, by rolling a prosthetic sheet on itself about 360° and connecting the two adjacent edges of the sheet.

The sheet which constitutes the part 2 is of circular shape. It is attached at its center to the tip of obturator 1 by adhesive or heat-sealing 4. This attachment by adhesive or heat-sealing can be carried out in such a way that said part 2 is slightly conical in shape and is coaxial with the obturator 1 and flares in the same direction as obturator 1.

By way of example, the plug-forming part 1 and the barrier-forming part 2 may be made of the same or different synthetic or natural material. The material(s) from which these parts are made is selected so as to be inert and infection-resistant, and to be biocompatable with tissue.

Numerous biocompatible absorbable and nonabsorbable materials can be used for parts 1 and 2. Suitable nonabsorbable materials for use in parts 1 and 2 include, but are not limited to, cotton, linen, silk, polyamides (polyhexamethylene adipamide (nylon 66), polyhexamethylene sebacamide (nylon 610), polycapramide (nylon 6), polydodecanamide (nylon 12) and polyhexamethylene isophtalamide (nylon 61) copolymers and blends thereof), polyesters (e.g polyethylene terephtalate, polybutyl terphtalate, copolymers and blends thereof), fluoropolymers (e.g expanded or not polytetrafluoroethylene) and polyolefins (e.g polypropylene including isotactic and syndiotactic polypropylene and blends thereof, as well as, blends composed predominately of isotactic or syndiotactic polypropylene blended with heterotactic polypropylene and polyethylene).

Suitable absorbable materials for use in parts 1 and 2 include, but are not limited to, homopolymers and copolymers of glycolide, lactide (which includes L-, D-, and mesoforms of lactide and mixtures thereof), ε-caprolactone, p-dioxanone, trimethylene, carbonate, 1.4-dioxepan-2-one, poly(alkylene axalate), and mixtures of such polymers with each other and with other compatible absorbable compositions as those described; for example, in U.S. Pat. No. 636,952 and U.S. Pat. No. 2,683,136.

The sheets that comprise parts 1 and 2 may be constructed in a variety of way and may be films, felts, knits, wovens, crochets, braided materials or combinations thereof. Numerous surgical meshes, nets or films have been described in the literature and reference may be made to U.S. Pat. No. 2,761,444; U.S. Pat. No. 3,054,406; U.S. Pat. No. 3,124,136;

U.S. Pat. No. 4,347,847; U.S. Pat. No. 4,633,873; U.S. Pat. No. 4,769,038; U.S. Pat. No. 5,092,884; U.S. Pat. No. 5,292,328; U.S. Pat. No. 5,569,273; PCT/GB95/01786 and EP 0 698 395 A1.

The conical structure forming the second part 2 has a greater expansion than the conical structure forming the first part 1, that means that the second part 2 forms a greater angle than the first part and has a greater radial size than the first part.

As an example of sizing, the obturator-forming cone-shaped part 1 may be 2.5 cm high with a diameter of 3 cm at its base, whereas the barrier-forming part 2 when at rest and in the absence of external stress, is 1 cm high with a diameter of 8 cm at its base.

Such a prosthesis obturating device is inserted in open surgery.

After dissecting the peritoneal sac and pushing it back into the (abdominal) hernial cavity, the surgeon presents the obturating device in front of the canal 3 of the hernia and places the tip of the conical part 1 directly facing said canal 3 (i.e concavity directed outside), then introduces the obturating device into said canal 3, such that the part 2 passes through to the inside of the wall in which is formed the canal 3 and is deployed by resilience, thus covering the internal orifice of the hernial canal, whereas part 1 obturates canal 3 being held in position in canal 3 by friction of its peripheral bordes at the vicinity of its base against the edges of orifice 3 by the way of some sutural points on part 1.

If need be, the surgeon may also suture the part 1 to hold it to the superficial orifice of canal 3.

The above-described structure is therefore very easy to put into place. It may be observed in particular that in this variant the barrier-forming part 2 positions itself appropriately, as soon as it is introduced into the hernial cavity, under the effect of its own resilience.

This structure is also very effective.

In particular, the slightly resilient shape of the barrier-forming part 2 contributes to holding the part 1 in the canal, because it bears against the inside face of the wall of the hernial cavity and thus opposes the natural tendency of the part 1 to escape outwards.

In addition, since it is positioned inside the hernial cavity and not on the outside, the barrier-forming part 2 provides excellent resistance to the abdominal pressure inside the hernial cavity.

A variant embodiment is shown in FIG. 3.

In the embodiment in FIG. 3, the conical part 1 is extended by a base 6, at least a part of which projects outwardly from said conical part 1, in a plane substantially perpendicular to the axis of said conical part 1. This base 6 is for bearing on the outside margin of the wall of the hernial canal. It facilitates suturing the obturating device by the surgeon.

In the example shown in FIG. 3, said base 6 is constituted by an annular collar which extends the part 1. In another variant, as shown in FIG. 4, it may also be constituted by a disk-shaped sheet fitted to the end of the part 1 that is remote from the part 2. In addition, shapes other than circular are of course possible. In particular, the base 6 may extend in one or more preferred directions as one or more tails which facilitate suturing in those areas.

What is claimed is:

1. A prosthesis obturating device to obturate a hernial canal, comprising:

a first part comprising a sheet material, said first part being adapted to obturate said hernial canal upon insertion of said obturating device in said hernial canal, a substantially conical second part comprising a sheet material fixedly attached to said first part, said second part being adapted to provide a barrier at an internal orifice of said hernial canal upon insertion of said obturating device in said hernial canal, wherein, upon insertion of said obturating device in said hernial canal, said first part is positioned within a hernial cavity and extends through said hernial canal, thereby obturating said hernial canal, and said second part is positioned within a hernial cavity, thereby forming a barrier at the internal orifice of said hernial canal.

2. A device according to claim 1, wherein the first part is hollow.

3. A device according to claim 1, wherein the first part is cylindrical or conical.

4. A device according to claim 1, wherein the first part is formed by rolling a prosthetic sheet on itself about 360° and connecting two adjacent edges of the rolled sheet.

5. A device according to claim 1, wherein the first and the second parts are formed of concentrical conical structures having concavity directed in the same direction.

6. A device according to claim 5, wherein the conical structures forming the first and the second parts are connected at tips of said conical structures.

7. Device according to claim 5, wherein the conical structure forming the second part has a greater expansion than the conical structure forming the first part.

8. A device according to claim 6, wherein the first part is extended at an end opposed to the second part by a base, at least part of which projects outwards from said first part in a plane substantially perpendicular to the axis of said first part.

9. A device according to claim 1, wherein at least one of the first and second parts is made from a non-absorbable material.

10. A device according to claim 9, wherein said non absorbable material is selected from the group consisting of cotton, linen, silk, polyamides, polyesters, flouropolymers and polyolefins.

11. A device according to claim 10, wherein said non absorbable material is selected from the group consisting of polyhexamethylene adipamide, polyhexamethylene sebacamide, polycapramide, polydodecanamide, polyhexamethyleneisophtalamide, polyethylene terephtalate, polybutyl terphtalate, polytetraflouroethylene, polypropylene including isotactic and syndiotactic polypropylene, blends composed predominately of isotactic or syndiotactic polypropylene blended with heterotactic polypropylene and polyethylene, and blends thereof.

12. A device according to claim 1, wherein at least one of the first and the second parts is made from an absorbable material.

13. A device according to claim 12, wherein said absorbable material is selected from the group consisting of homopolymers and copolymers of glycolide, lactide including L-, D-, and mixtures, ε-caprolactone, p-dioxanone, trimethylene carbonate, 1,4-dioxepan-2-one, and poly (alkyleneoxalate).

* * * * *